US011284667B2

(12) United States Patent
Chen et al.

(10) Patent No.: US 11,284,667 B2
(45) Date of Patent: Mar. 29, 2022

(54) FOOTWEAR CONSOLE

(71) Applicants: Shyi Yuan Chen, Diamond Bar, CA (US); Rosa Chen, Diamond Bar, CA (US)

(72) Inventors: Shyi Yuan Chen, Diamond Bar, CA (US); Rosa Chen, Diamond Bar, CA (US)

( * ) Notice: Subject to any disclaimer, the term of this patent is extended or adjusted under 35 U.S.C. 154(b) by 0 days.

(21) Appl. No.: 16/564,544

(22) Filed: Sep. 9, 2019

(65) Prior Publication Data
US 2021/0145111 A1    May 20, 2021

(51) Int. Cl.
| *A43B 3/00* | (2022.01) |
| *A43B 7/04* | (2006.01) |
| *A43B 3/38* | (2022.01) |
| *H01Q 9/04* | (2006.01) |
| *H01Q 1/27* | (2006.01) |
| *H02J 7/02* | (2016.01) |
| *H02J 50/00* | (2016.01) |
| *H02J 50/27* | (2016.01) |
| *H02J 50/12* | (2016.01) |
| *H02J 50/40* | (2016.01) |

(Continued)

(52) U.S. Cl.
CPC .................. *A43B 3/38* (2022.01); *A43B 3/35* (2022.01); *A43B 3/36* (2022.01); *A61B 5/02055* (2013.01); *A61B 5/6807* (2013.01); *A61F 7/02* (2013.01); *G16Y 10/75* (2020.01); *H01Q 1/273* (2013.01); *H01Q 9/0407* (2013.01); *H02J 7/02* (2013.01); *H02J 50/001* (2020.01); *H02J 50/12* (2016.02); *H02J 50/27* (2016.02); *H02J 50/402* (2020.01); *A61B 5/021* (2013.01); *A61B 5/02438* (2013.01); *A61F 2007/0047* (2013.01); *A61F 2007/0233* (2013.01); *G06F 3/147* (2013.01); *H04R 19/04* (2013.01)

(58) Field of Classification Search
CPC ....... A43B 3/0015; A43B 3/0005; A43B 3/35; A43B 3/36; A43B 3/38
See application file for complete search history.

(56) References Cited

U.S. PATENT DOCUMENTS

| 2013/0020986 A1* | 1/2013 | Linzon ................. A43B 3/0015 320/107 |
| 2016/0051006 A1* | 2/2016 | Dakhil ..................... A43B 7/02 36/44 |

(Continued)

FOREIGN PATENT DOCUMENTS

CN        105495824 A    *    4/2016

OTHER PUBLICATIONS

Stan Horaczek; Xiaomi's long-range wireless charger shows a glimpse of a cord-free future; Popular Science, online article; https://www.popsci.com/story/technology/xiaomi-long-range-wireless-charging/; accessed Jul. 28, 2021; published Feb. 1, 2021. (Year: 2021).*

*Primary Examiner* — Daniel J Colilla (57) ABSTRACT

Presenting a new approach to architect footwear as a communication and energy-transporting platform for personalized smart living. This is done by integrating the most advanced technologies today, along with some known technologies still under development, to provide solutions to power on demand for all personal and wearable devices.
The systems, methods, and apparatuses disclosed in this invention make our personal and wearable devices smarter, thereby providing higher practical functions and more efficiency to our everyday lives.

7 Claims, 8 Drawing Sheets

(51) Int. Cl.

| | |
|---|---|
| *A61B 5/00* | (2006.01) |
| *A61B 5/0205* | (2006.01) |
| *A61F 7/02* | (2006.01) |
| *G16Y 10/75* | (2020.01) |
| *A43B 3/35* | (2022.01) |
| *A43B 3/36* | (2022.01) |
| *H04R 19/04* | (2006.01) |
| *G06F 3/147* | (2006.01) |
| *A61B 5/021* | (2006.01) |
| *A61B 5/024* | (2006.01) |
| *A61F 7/00* | (2006.01) |

(56) References Cited

U.S. PATENT DOCUMENTS

| | | | | |
|---|---|---|---|---|
| 2016/0066818 A1* | 3/2016 | Cowley | ............... | A43B 3/0005 |
| | | | | 600/592 |
| 2016/0316849 A1* | 11/2016 | McLeod | ............... | A43B 21/24 |
| 2020/0072319 A1* | 3/2020 | Sharpes | ............... | A43B 21/30 |

* cited by examiner

Antenna Structure and Materials

Antenna Energy Harvest 8.1

FOOTWEAR CONSOLE

BACKGROUND

The current footwear in the market place has not been able to address the needs to combine its functionalities to accommodate today's sophisticated demands for a better living. People need to have solutions for color/imaging styling, long self-generating power, wireless charging to all personal devices, free access to the internet without battery, safety lighting while walking, and ultra-high security payment by acoustic communication.

The invention is to solve the needs by integrating advanced technology to generate enough power by (1) walking while transmitting the power wirelessly to all the personal or Internet Of Things (IOT) devices from 0 to 50 meters around the person wearing the footwear or by (2) receiving energy from the ambient wirelessly using special designed antenna with crystal arrays amplify and post charging devices for nearby devices with wires connections.

BRIEF SUMMARY OF THE INVENTION

Architect a new platform of footwear as a communication and modern life living console that can generate power and transmit this power either wirelessly or with wires to such items: batteries, cell phones, wearable electronic devices, all the Internet Of Things (IOT), heating and cooling in the shoe pad, LED lights, power banks, cooking ware, and speakers and microphones.

BRIEF DESCRIPTION OF THE DRAWINGS

3.2 shows many industries can benefit from such wireless charging devices to drastically improve life quality once the standard for 3.1 can be established for power receiving modules on each and every device mentioned.

3.3 presents the reality of our daily wear inside and out with smart textiles, fabrics, and cloths with such wireless charging without a battery. This provides more convenience and efficiency with the devices we access every day. It also paves the foundation for color and pattern styling changes that will be presented in the digital fashion that is likely to immerge in the next few decades or centuries.

3.4 reveals that the infrastructure built from 3.0, 3.1, 3.2, and 3.3 prove that personal artificial intelligence enabled wearables is plausible and practical in all wearable items of the near future. These wearable items can become a platform not just for environmental friendly living but also an on demand application for smart cloud, smart entertainment, smart health management, smart driving, smart energy, smart business, smart contract, smart financials, and smart government etc.

3.5 shows the personalized smart living platform will be a reality when the above points can be achieved overtime from the footwear console to integrate device level 3.0, 3.1, 3.2, and subsystem level 3.3 and 3.4.

DETAILED DESCRIPTION OF THE INVENTION

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice of the invention, the exemplary methods, devices and materials are now described.

All publications mentioned are incorporated by reference for the purpose of describing and disclosing. For example, the designs and methodologies described in the publications might be used in connection with the presently described invention. The publications listed or discussed above, below, and throughout the text are provided solely for their disclosure prior to the filing date of the present application. Nothing herein is to be construed as an admission that the inventors are not entitled to antedate such disclosure by virtue of prior invention.

As used in the description herein and throughout the claims that follow, the meaning of "a", "an", and "the" includes reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to. As used in the description herein and throughout the claims that follow, the meaning of "in" includes "in" and "on" unless the context clearly dictates otherwise.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the embodiments. As used herein, the term "and/or" includes any and all combinations of one or more of the associated listed items.

Figure 1:
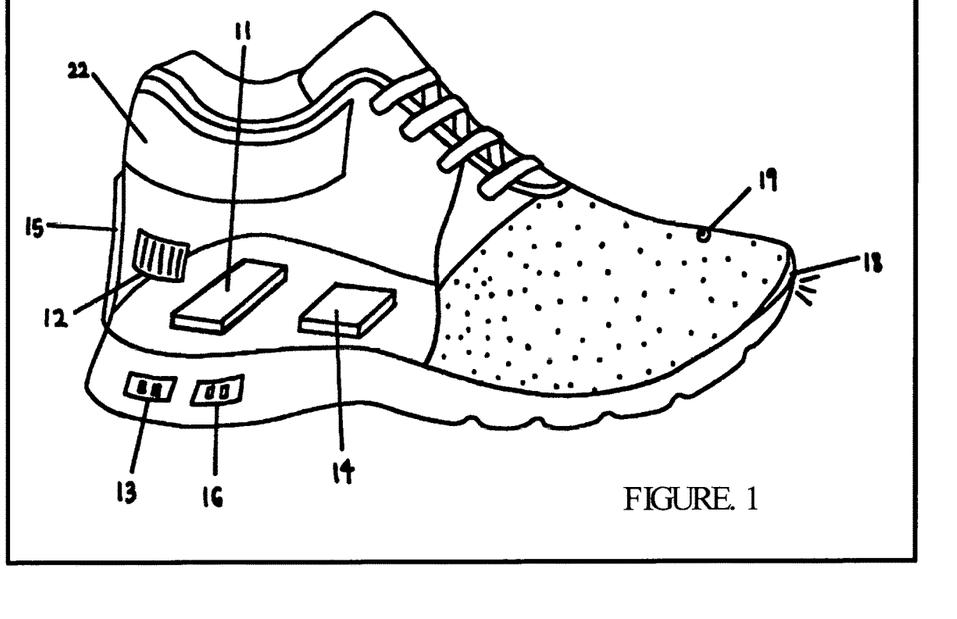
FIG. 1 shows the infrastructure of the Footwear Console invention, where 11 is the automatic rotational magnetic trigger power generator ranged from 0.1 to 200 watts power harvest capacity. 15 is the remote transceiver power device that can receive power from 11 and/or from ambient which can transmit the power wirelessly or with wires to all the Footwear Console components and the device around 0-50 meters range which needs power charges. 12 is the RF communication module, 13 is the external power connector, 16 is the USB connector, 14 is a rechargeable battery, 22 is a flexible roll able display, 19 is low power LED chips that can form the color changes according to users experience for styling and personal mood in a daily life. 18 is the focus LED light that can reach 0.1-20 meters long for user's safety while walking or riding a bicycle in the night.

In this invention, the FIG. 1 presents a footwear console which comprises an integrated solution for power harvesting devices having rotational magnetic trigger power generator 11, a power transceiver 15 that can receive power from 11 or from the ambient and transmit such power to all the components in and out of footwear console on demand.

The power generating range from 0.1 to 200 watts at a radiation range of 0-50 meters away from the footwear console can charge the battery of any personal or mobile devices and similar electronic or bio-electronic devices.

It also comprises a rechargeable battery 14 and electric power connector 13, USB connector 16, as well as many small lower power LED chips 19 or similar that can change the colors of any footwear and future wearable fabrics and cloths for personal styling. 18 depicts an LED focus light which enables greater levels of safety while walking or riding a bicycle at night.

Figure 2:
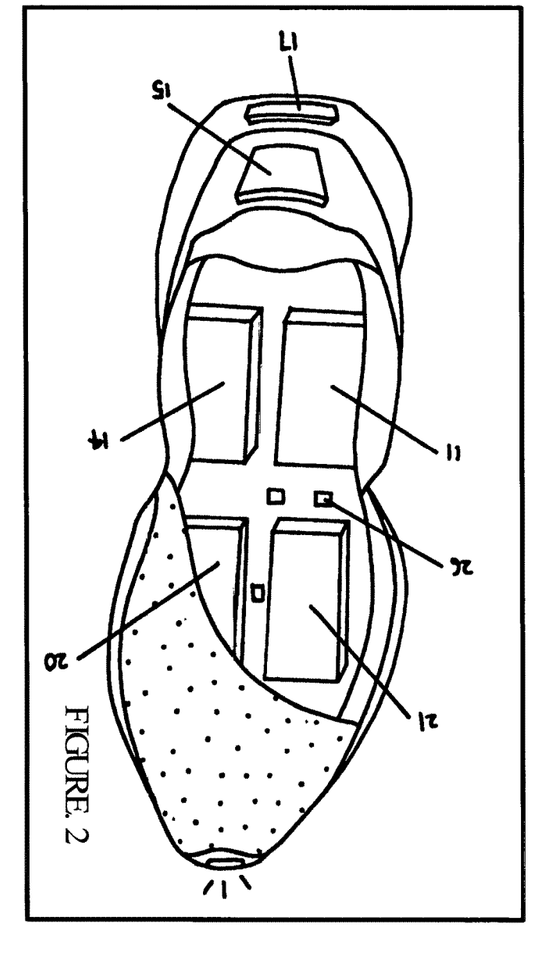
FIG. 2 illustrates the ideas of putting acoustic communication technology (17) to extend the safety and security features to protect people dressed in personal wearable devices. 21 depicts a thermal heating and cooling device that provides user comfort level wearing such footwear. The 20 is the CPU and controller for monitoring pressures, temperatures, heart beat rates, energy harvesting, and wireless energy transmitting controls on demand to create a user smart living platform outlined in FIG. 3.

FIG. 2 presents the inside of the footwear that is comprised of a CPU and controller 20 and sensors 26 for measuring body temperature, blood pressure, heart rate, and sweat for all body bio physical situations, as well as controlling the power harvesting and dispensing through the whole footwear console.

With the highly efficient rotational magnetic trigger power harvesting technology, the energy for cooling and heating inside the insole of the footwear shoe becomes a reality, which can even create a pressure differences to evacuate the air from inside to the outside of the footwear. This will drastically increase the functionality and quality of footwear.

Figure 3:
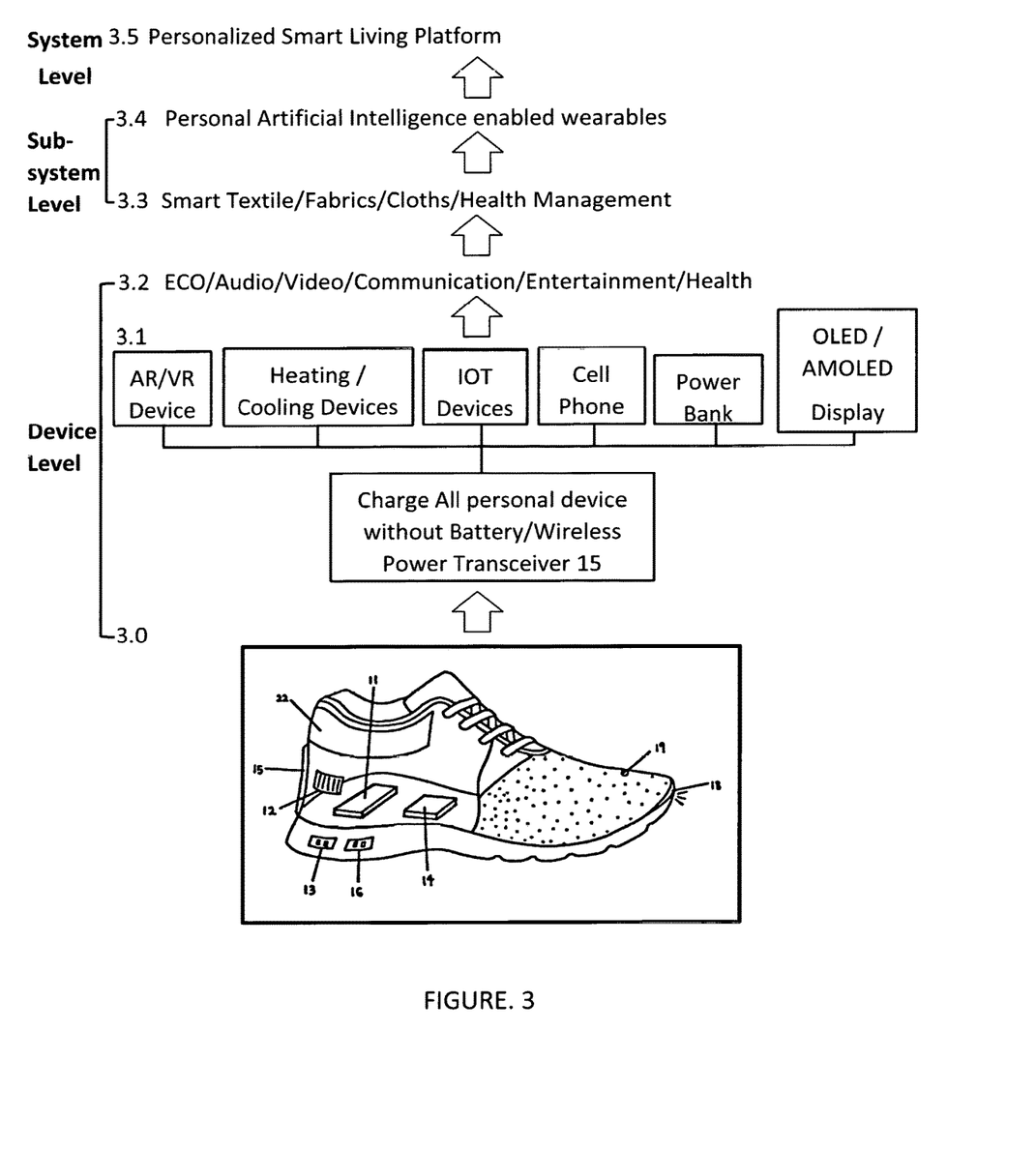
FIG. 3 presents the whole invention platform by such Footwear Console using very high efficiency power harvesting, wirelessly receiving and transmitting devices ranged from 0.1 to 200 watts at a radiation range from 0-50 meters. 3.1 shows mobile or personal devices as depicted can be charged without using a rechargeable battery and constitutes battery hunger devices by a real remote wirelessly power charge that can have high enough energy transferred wirelessly to a long distance; around 0-50 meters range from the footwear console.

This invention also architects a personalized smart living platform described in FIG. 3 Establishing the ideas to generate and transmit power wirelessly from wearing a footwear as a console to harvest, control, and dispense power to all devices around our body. This footwear console can be treated like an individual cell phone tower, meaning every one of us can become an individual signal pole of conducting and communicating W-Fi or Satellite signals to create a powerful communication cell of smart "everything" in our daily life.

This invention also covers a state of art technology that can communicate personal information and data in secure and safe ways by a unique innovative acoustic communication methodology; including but not limited to GI-WI standard by using the world's most advanced speakers and microphones better than 94-120 dB to simulate loud and clear communication by acoustics. In such a way, there is no need to worry about the potential damage of the high frequency RF communication to brains, ears, eyes like cell phones and similar devices when used for long periods of time.

The power required for an Analogue MEMS Microphone in this invention should be in the range of 0.07 u Amp to 0.5 u Amp, which is 100-500 times lower in power consumption than today's best microphones, which are 16-60 u Amp.

When applying a Digital MEMS Microphone for this footwear console should be less than 1.5 u Amp—that is a 100-400 times lower power consumption than the best Digital Microphones in the market as of today, which consume 190-600 u Amp. The result is to extend the battery life of current Bluetooth communication from 8-10 months to 8-10 years. In addition, using Microphone Modem for communication in this invention can cover the signal range from 0-150 meters without distortion for all personal mobile and Internet devices.

Flexible Thin Roll able display of AMOLED/OLED or TFT Micro LCD is depicted as 22, which can be operated by chargeable battery or directly from wireless power from 15 and can become a mobile computer using 14 as a CPU and Controller. The Augmented Reality/Virtual Reality device described in 3.1 can also receive power from 15 on demand without carrying a chargeable battery embedded in the Augmented Reality/Virtual Reality.

The device level of footwear console depicted in 3.1 of FIG. 3 can be enabled by establishing a wireless charging standard interface to receive power from 15 without battery, such that all the device level can be free of cables connecting to each other, where the reality of Internet of things devices can be broadly applied among all the industries.

When the device level of 3.1 can be implemented, a new era of industries stated in 3.2. will be launched for Sports, Communication, Entertainment, Health Management, Audio/Video, and other industries such as Electronics, Mechanical, Biopharmaceutical, Chemicals, and Medical applications. 3.2 describe a next level of 3.1 as an integrated device level of the Footwear Console, which comprise of 3.0, 3.1, and 3.2.

The footwear console creates the foundation of wearable devices based on 3.3 by applying Nano carbon tubes of fibers as a raw material to form smart textile, fabrics, and cloths to become hundreds of thousands of sensors to get personal bio data real time to health care management centers for doctors' review.

The wireless power-transceiver device 15 can transform the values of sports and fashion industries by allowing customizable changes to the colors and styles at a programmable scale utilizing smart textile and fabrics/cloths.

Personal Artificial intelligence enabled wearable items can be extended to the future of styling, comfort, business, entertainment, and health management platforms. For example, they can offer Augmented Reality/Virtual Reality, smart voice command to achieve a 94-120 dB level of clarity in acoustic transmitter and receiver to link internet of everything devices. They can further implement hundreds of applications in diapers for kids and adults whom require timely and safety living assistance. Thus, these personal artificial intelligence enabled wearable items can be applied to all the wearable devices, which normally need a battery to operate, now without a charger or tedious cables/connectors to facilitate a cable free environment.

With the application of 3.0, 3.1, 3.2, 3.3, and 3.4 in place, some or all parts are implemented. The personalized smart living platform depicted as 3.5 reveals that our daily life can have all kinds of smart "everything" available in the market place, as well as a much higher living standard and quality of life embedded in this system.

Figure 4:
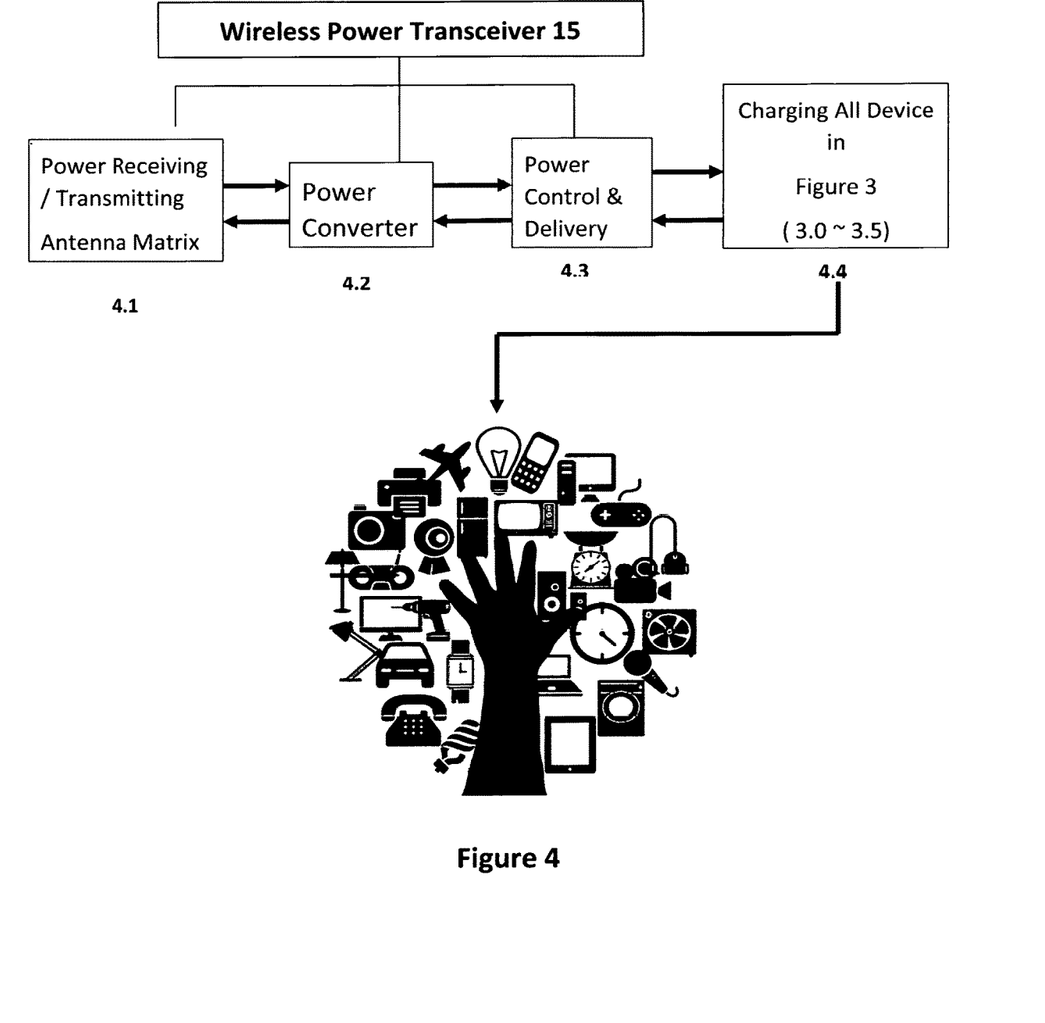
FIG. 4 is a block diagram of the wirelessly energy charging from an antenna receiver to a power transmitter (4.1.) through power converter (4.2.) and power control/distribute circuit (4.3) which the power lands to the final devices to be charged (4.4.)

The invention of a wireless power transceiver 15 in FIG. 2 comprises of power receiving antennas 4.1, as depicted in FIG. 4, and a power converter 4.2, power control and delivery4.3. Power receiving antennas 4.1 absorb the energy from 11 and the ambient by the form of all kinds of electromagnetic waves, air electrons by RF waves, invisible Alpha, Gamma rays, and quantum energy generated from the surrounding where the energy can only be continuously absorbed under the conditions of impedance match between 4.1. and 4.2. and 4.3. versus the balance of the load devices depicted in 4.4.

Figure 5:
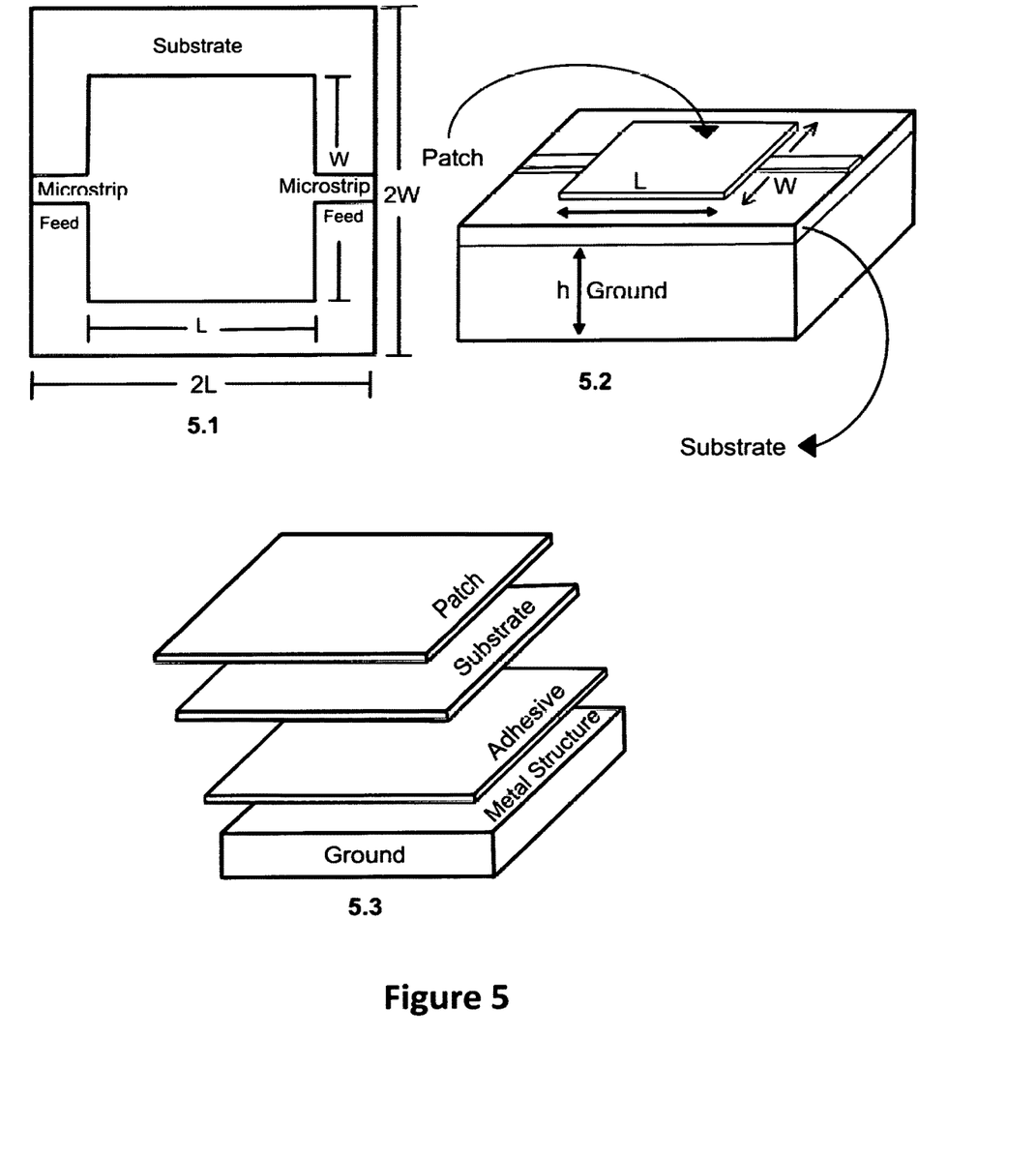
FIG. 5 depicts the substrate structure of the wireless charging antenna where 5.1. is the top view of the antenna patch and 5.2. is the perspective view of the structure. 5.3. is the exploded view of the antenna substrate structure.

The structure of the Antenna 4.1 is outlined per FIG. 5 but it does not have to be limited to this specific structure. 5.1. is the top view of the antenna patch, where L and W can be ranged from 10 micrometer- to 2000 micrometer in a semiconductor substrate for 0.1 micro watt to 1.0 watt application with "h" dielectric less than 500 micrometer, and/or L and W ranged from 0.5 centimeter to 200 centimeter from 0.5 watt to 50 Watts power application with "h" dielectric from 501 micrometer to 0.2 cm, and/or L and W greater than 200 centimeter up to 10 meter for high power application with "h" dielectric 0.21 cm to 10 cm in thickness.
The side view of the said antenna is depicted as 5.2 and the exploded view 5.3. shows the detail of the structure where it can be multilayer sandwiched to meet any combinations of impedance control requirement from the system in FIG. 4.

Figure 6:
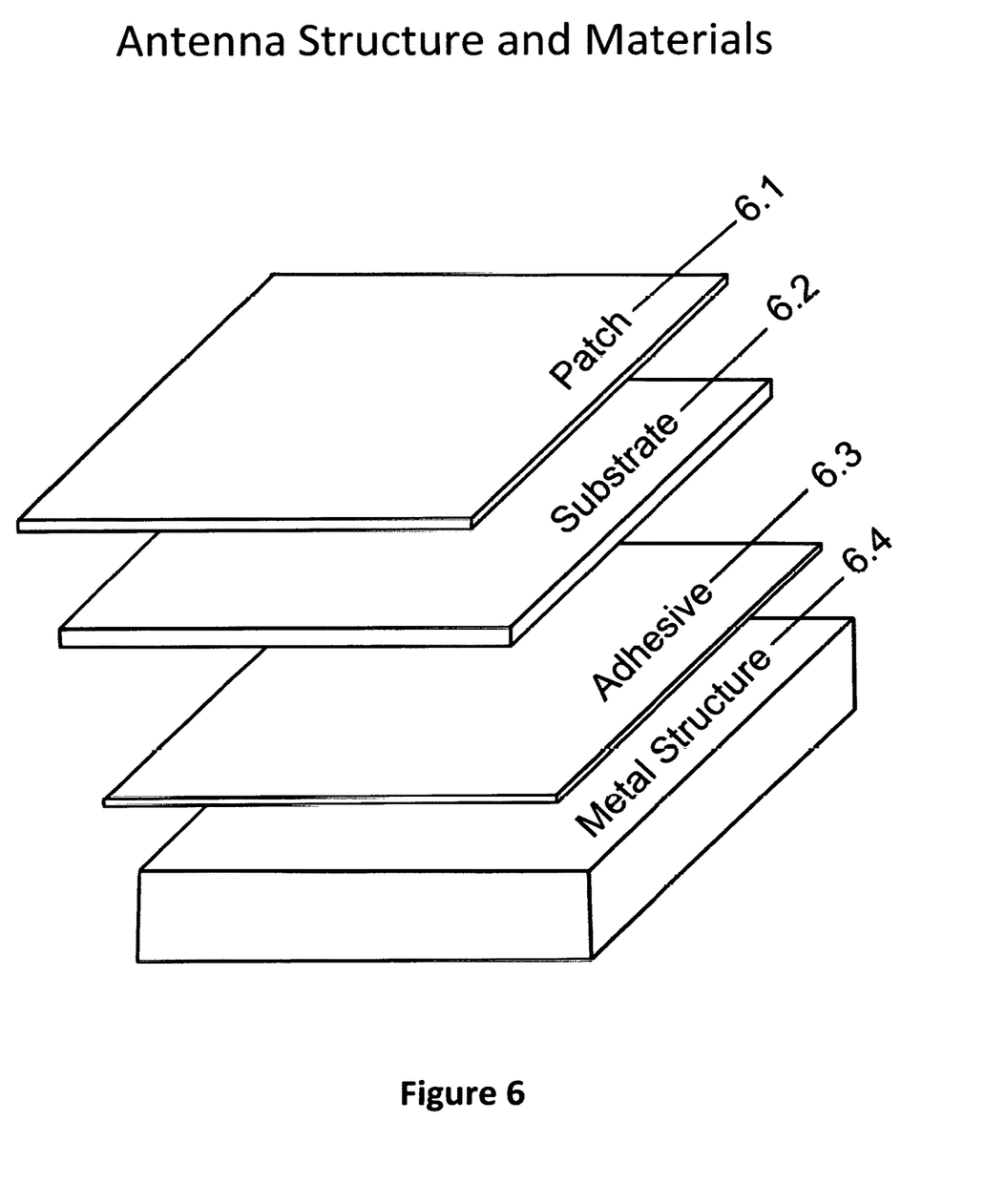
FIG. 6 shows the specific materials used for patch 6.1., substrate 6.2., adhesive layer 6.3., and ground layer 6.4.

The materials of the structures of such Antenna are listed in FIG. 6. The patch material 6.1. can use copper, beryllium copper, aluminum, Silicon, GaAs, Tungsten, Vanadium, Cobalt which the thickness ranged from 0.001 micron meter to 2.0 centimeter ranged for respective low, medium and high power transceiver applications.
The substrate depicted in 6.2 use material of insulation material with great thermal conductivities such as Phenolic Resin FR4, Polyimide, aluminum nitride, silicon nitride, beryllium nitride that can carry signals and power frequency ranged from 0.01 hz to 1,000 Giga hertz.
The adhesive layer per 6.3 can apply PVA (Poly Vinyl Acetate). Polyurethane, Ethyl Cyanoacrylate, Phenol formaldehyde, Butyl rubber, Dextrin etc. The materials and structures of such Antenna are listed in FIG. 6 but it does not have to be limited to the specified.
The 6.4 in FIG. 6 describe the ground materials which are metals including Aluminum, Au, Bronze, Copper, Silver, Palladium, Zinc, Nickel, Platinum, or any conductive sputtering materials that can meet the specific impedance and functional system requirement per FIG. 4.

Figure 7:
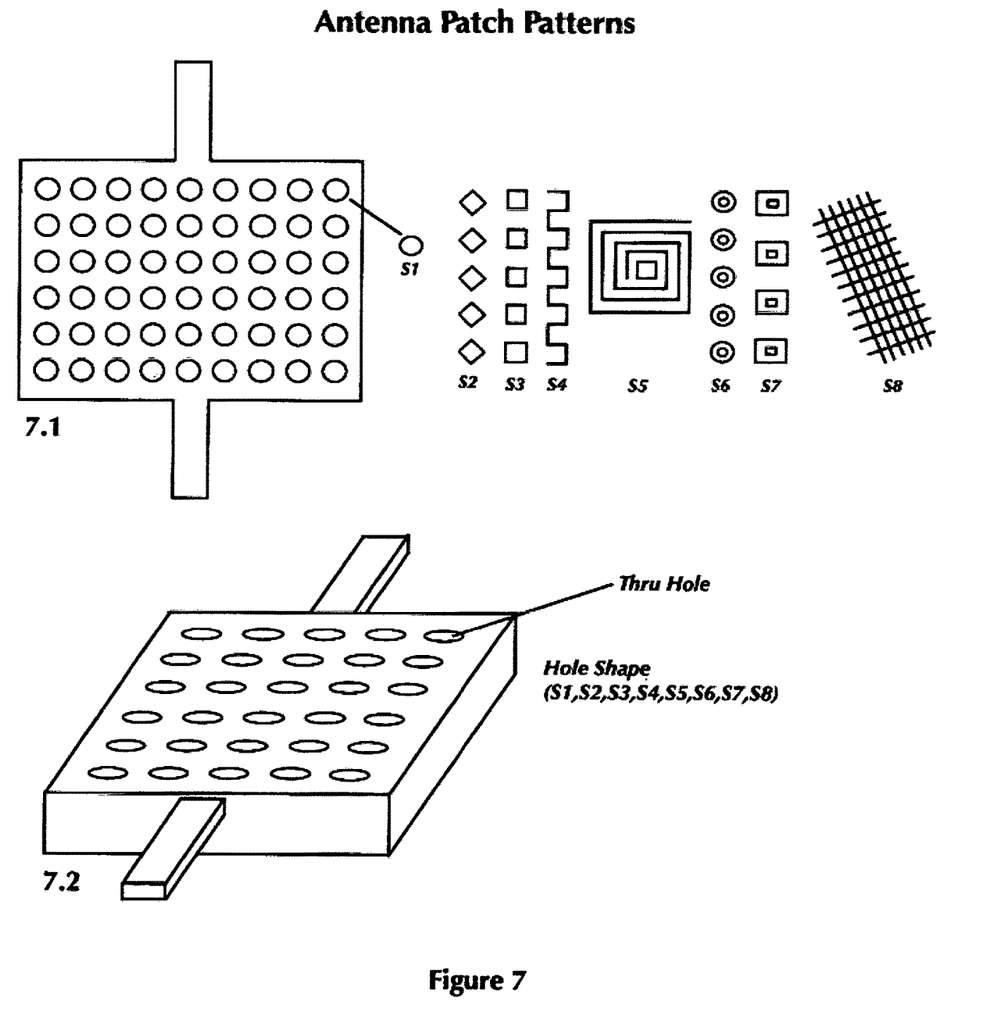
FIG. 7 depicts the various patterns of the antenna patch layer used for this invention. 7.1.1s the top view where s1,s2,s3,s4,s5,s6,s7,s8 is the through hole pattern on the patch and 7.2 is the 3D view of the patch.

The patterns depicted in FIG. 7 of the antenna patch varies depending on the impedance match inside of 4.1 and among 4.1. and 4.2,4.3,4.4 so that a maximum energy can be harvested. The patterns should not be limited to S1, S2, S3, S4, S5, S6, S7, S8. It also covers the combination of any of the patterns depicted in FIG. 7 in order to get optimized energy harvest in the system stated above.

Figure 8:
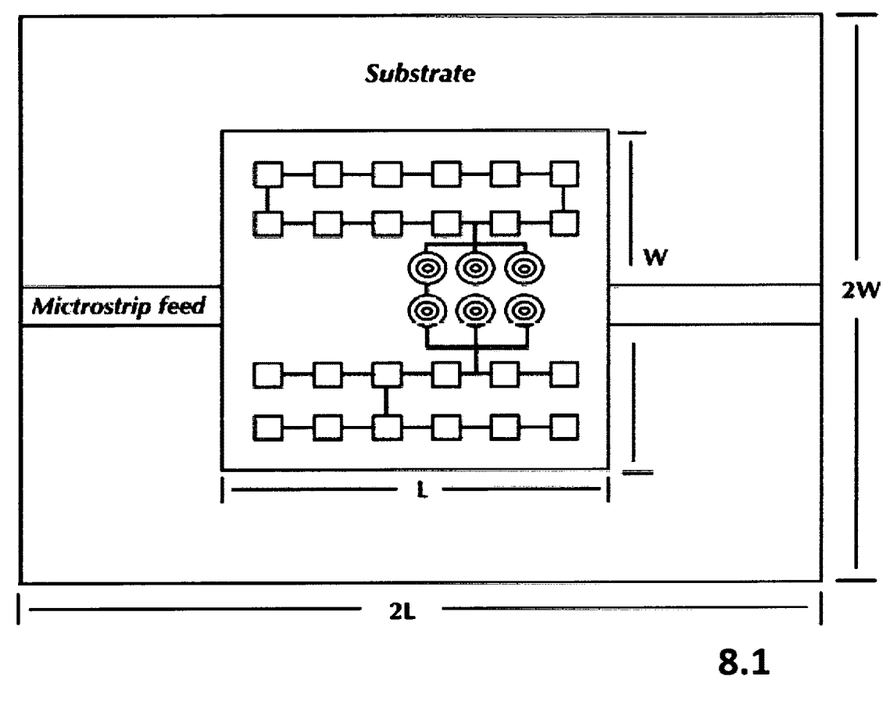
FIG. 8 shows the energy harvest by antenna through a special arrangement of a matrix of electromagnetic coils placed on the antenna patch. 8.1.1s the top view of the coils sitting on the antenna patch and 8.2. is the perspective view of the coil matrix in relation to the antenna substrate and ground layers.
Figure 9:
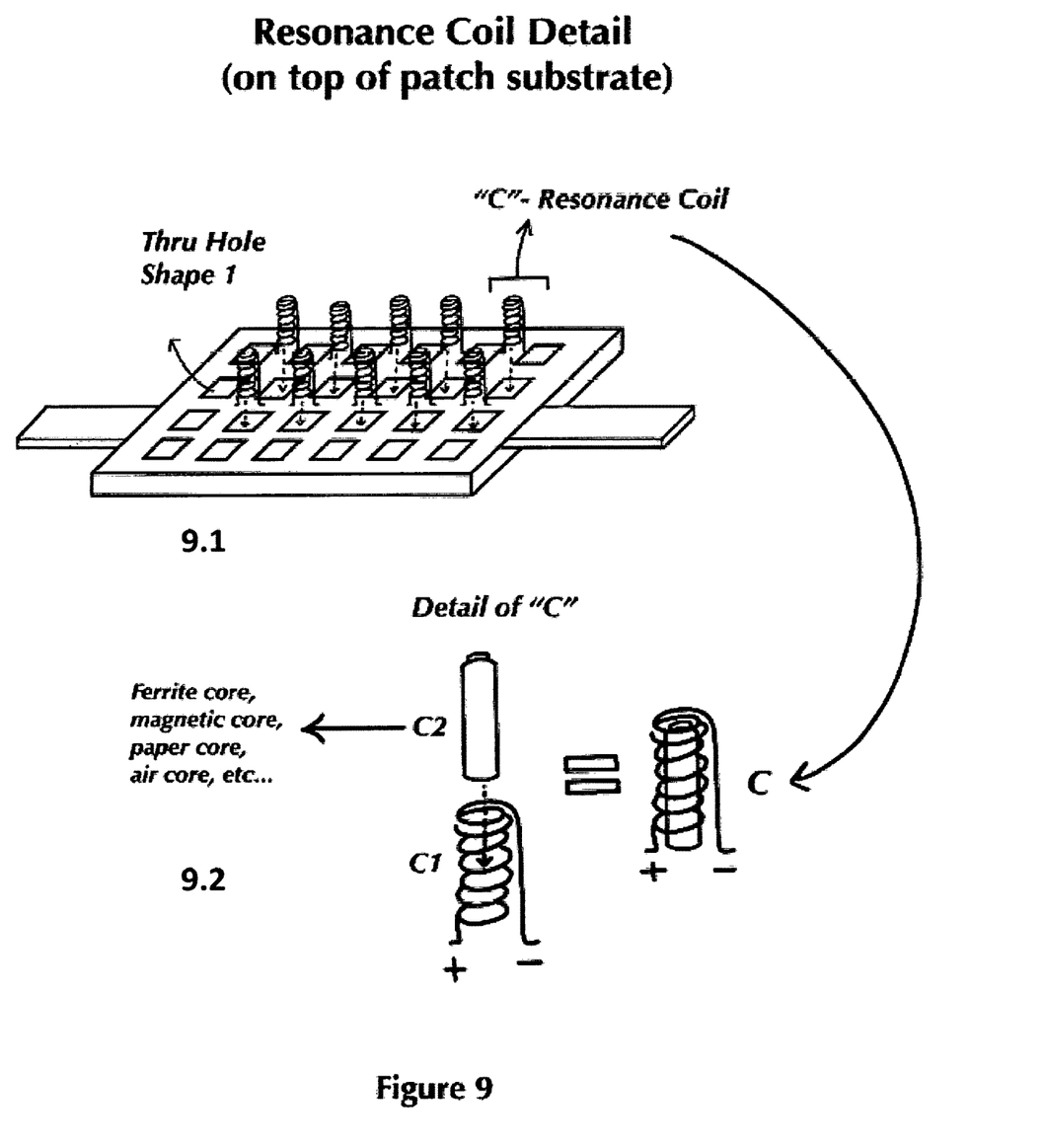
FIG. 9 depicts the resonance coils matrix detail on top of the antenna patch 9.1. and the detail coil structure with different core materials on 9.2.

The antenna receiving and transmitting matrix signal power per 4.1. is achieved by combining the structure FIG. 6 with patch patterns depicted in FIG. 7 and energy harvest resonance coil per FIG. 8. The resonant frequency can be generated by both in the energy harvest coil and the patch patterns and materials of the Antenna to create a vertex energy flow by matching the impedance of 4.2, 4.3 and 4.4. such that the receiving energy can be boosted up by power converter 4.2 and deliver the power through power control 4.3. to the load device 4.4.

The resonant coil matrix depicted in 8.1 and 8.2 connecting to the patch 6.1 in the form of 2×2, 4×4, 6×6, 8×8 up to n×n (n<=500,000) array matrix. The coil diameter ranges from 10 micron meter to 50 centi-meter and the wire used to form the resonant coil is made out of the materials from copper, beryllium copper, bronze, nickel, aluminum, tungsten, titanium, cobalt, platinum, gold, silver, zinc, or magnesium, with a wire diameter ranged from 1.0 micron meter to 0.5 centimeter depending on very low power in semiconductors or low power in cell phone, personal mobile device wireless charging application or high power energy harvest devices.

Inside of the coil is a magnetic conductive core made out of ferrite, permanent magnet, ceramics, synthetic paper, resins, plastics, air, etc. with the inductance value ranges from 0.01 to 100 henry.

The power converter 4.2 in FIG. 4 is comprised of different frequency of Crystal Oscillator arrays with a range from 0.5 Hz to 1,000 GHZ and the structures of the arrays are conforming to the resonant coil matrix stated above and per FIG. 8. In addition to the Crystal Oscillator arrays, it also includes frequency filter, transformer, current voltage regulator which the details are not shown in the drawing of 4.2.
The crystal oscillator arrays is couple with the antenna resonance coil 8.2 in FIG. 8 to deliver an optimized power harvest on this invention based on its unique range of the sizes and materials and patterns to be used for a particular device design such as cell phone, Power bank charger, mobile personal device, uninterrupted power supply, personal cell tower, LED Lighting, fashion wearable, etc.

The whole wireless transceiver per FIG. 4 is configured with all the necessary electric circuit and electronic/magnetic components in a shielding enclosure which does not show on the drawing where it can apply soft bendable and water proof and hazardous environment resistance materials to realize the application of this Footwear Console invention.

What is claimed is:
1. A footwear platform configured as a communication and modern life console, said footwear platform comprising:
    an article of footwear;
    a power generator configured to harvest power generated by movement of the footwear;
    a power transceiver configured to receive or transmit power wirelessly;
    a rechargeable battery;
    a USB connector;
    an external power connector;
    an RF communication module;
    a plurality of color-changeable LED chips arranged on a surface of the footwear, said color-changeable LED chips configured to display colors according to a user's style or mood; and an LED focus light arranged at a toe end of the footwear and configured to illuminate an area in front of the footwear.

2. The footwear platform, according to claim 1, further comprising:
a plurality of sensors each sensor configured to monitor a respective one of body temperature, blood pressure, and heart rate; and
a CPU configured to control energy harvesting and wireless energy transmission and monitor the body temperature, blood pressure, and heart rate sensed by the sensors.

3. The footwear platform according to claim 1, further comprising:
a flexible, thin, rollable display comprised of an AMO-LED/OLED display or TFT micro LCD configured to be powered by the rechargeable battery or directly from the wireless power transceiver.

4. The footwear platform, according to claim 3, further comprising:
a thermal heating and cooling device.

5. The footwear platform, according to claim 1, wherein the power transceiver further comprises:
a power receiving antenna patch on a semiconductor substrate with a length and width each in the range of 10-2000 micrometers.

6. The footwear platform, according to claim 5, wherein the power receiving antenna patch comprises any one of copper, beryllium copper, aluminum, Silicon, GaAs, Tungsten, Vanadium, Cobalt.

7. The footwear platform, according to claim 1, further comprising:
a power converter comprising different frequencies of crystal oscillator arrays with a frequency range from 0.5 Hz to 1,000 GHZ, wherein the power converter is coupled to the power transceiver.

* * * * *